United States Patent [19]

Shah et al.

[11] Patent Number: 5,705,330
[45] Date of Patent: Jan. 6, 1998

[54] CHEMILUMINESCENT IMMUNOASSAY FOR ANTIBODY DETECTION

[75] Inventors: Dinesh O. Shah, Libertyville; Russell B. Richerson, Barrington, both of Ill.

[73] Assignee: Abbott Laboratories, Abbott Park, Ill.

[21] Appl. No.: 422,404

[22] Filed: Apr. 14, 1995

[51] Int. Cl.$^6$ .................................................. G01N 33/576
[52] U.S. Cl. ........................... 435/5; 435/7.92; 435/975; 436/518; 436/172; 436/805; 436/808
[58] Field of Search ............................. 435/5, 7.2, 7.92, 435/968, 975, 974; 436/513, 518, 524, 533, 538, 541, 172, 808

[56] References Cited

U.S. PATENT DOCUMENTS

| | | | |
|---|---|---|---|
| 4,228,237 | 10/1980 | Hevey et al. | 435/5 |
| 4,469,787 | 9/1984 | Woods et al. | 435/7.4 |
| 4,927,769 | 5/1990 | Chang et al. | 436/518 |
| 4,935,339 | 6/1990 | Zahradnik | 435/5 |
| 4,959,182 | 9/1990 | Schaap | 252/700 |

FOREIGN PATENT DOCUMENTS

| | | |
|---|---|---|
| 0160900 | 11/1985 | European Pat. Off. . |
| 9208979 | 5/1992 | WIPO . |

OTHER PUBLICATIONS

W. Rudolf Seitz, "Chemiluminescence & Bioluminescence", *Clinical Biochemistry*, vol. 17, Apr. 1984 pp. 120–125.

I. Bronstein, et al., "1–2–Dioxetanes: Novel Chemiluminescent Enzyme Substrates. Applications to Immunoassays", *Journal of Bioluminescence and Chemiluminescence*, vol. 4, pp. 99–111 (1989).

D. Shah, et al., "Acridinium–Labeling to Latex Microparticles and Application in Chemiluminescence–Based Instrumentation", *Clinical Chemistry*, vol. 40, No. 9, (1994).

J. Wolf–Rogers, et al., "A chemiluminescent, microparticle–membrane capture immunoassay for the detection of antibody to hepatitis B core antigen", Journal of Immunological Methods, 133 (1990) 191–198 Elsevier.

*Primary Examiner*—Lora M. Green
*Attorney, Agent, or Firm*—Cheryl L. Becker; Priscilla E. Porenbski

[57] ABSTRACT

A chemiluminescent assay utilizing a precomplex reagent of a probe comprising an enhancer compound such as a hapten and a conjugate comprising a chemiluminescent signal generating compound. Kits for performing such an chemiluminescent assay are also provided.

9 Claims, 6 Drawing Sheets

CHEMILUMINESCENT IMMUNOASSAY FOR ANTIBODY DETECTION

BACKGROUND OF THE INVENTION

This invention relates generally to immunoassays for detection of antibodies utilizing chemiluminescent compounds, and more particularly, relates to chemiluminescent immunoassays to detect antibodies wherein a precomplex mixture is formed and a two-step assay is performed, resulting in greater signal.

Immunoassays that employ chemiluminescent labels as the signal generating compound are known. The application of chemiluminescence generation and detection for immunoassays has been reviewed by W. R. Seitz, "Immunoassay Labels Based on Chemiluminescence and Bioluminescence," *Clinical Biochemistry* 17:120–126 (1984).

A method for performing a chemiluminescent assay involving directly exciting and measuring a chemiluminescent signal emanating off an immune complex immobilized on or in a solid, porous element that is used as a separation means in a heterogenous immunoassay and an apparatus for performing this measurement are described in pending U.S. patent applications Ser. No. 07/425,643 now U.S. Pat. No. 5,089,424 and 07/206,645 now abandoned which enjoy common ownership and are incorporated herein by reference.

The generation of light as a result of a chemical reaction is known in the art and was reviewed by Schuster and Schmidt in "Chemiluminescence of Organic Compounds," V. Gold and D. Bethel, eds., *Advances in Physical Organic Chemistry* 18:187–238 Academic Press, New York (1982). The use of acridinium compounds as labels for immunoassays and subsequent generation of short-lived chemiluminescence signals from these labels has been described by I. Weeks et al., in "Acridinium Esters as Highly Specific Activity Labels in Immunoassays," *Clin. Chemistry* 19:1474–1478 (1984). The use of stable acridinium sulfonamide esters has been described in a co-owned and co-pending patent application by P. G. Mattingly et al., U.S. patent application Ser. No. 921,971, now U.S. Pat. No. 5,224,833 which is incorporated herein by reference and published as European Patent Application No. 0 273 115. The generation of long-lived luminescent signals has been described in the art as resulting from action of enzymes or nucleophilic agents on dioxetane compounds containing an adamantane structure. See, for example, published European Application No. 0 254 051 to A. P. Schaap; published P.C.T. Patent Application No. WO 8906650; I. Bronstein et al., "1,2-Dioxetanes, Novel Chemiluminescent Substrates, Applications to Immunoassays," *J. Bioluminescence and Chemiluminescence* 4:99 (1988) and the 5th International Conference on Bioluminescence and Chemiluminescence, Florence-Bologna, Italy, Sep. 25–29 (1988).

The use of a signal enhancer such as the use of avidin-biotin also is known. For example, U.S. Pat. No. 4,228,237 to Hevey et al. describes the use of a biotin labelled specific binding substance for a ligand used in a method which also employs an enzyme labelled with avidin. The use of a biotin-anti-biotin system is described in U.S. patent application Ser. No. 608,849 filed May 10, 1984, now abandoned which enjoys common ownership and is incorporated herein by reference (published on Nov. 13, 1985 as European Patent Application No. 160,900).

Methods of enhancing and amplifying the chemiluminescent signal generated in an immunoassay are known in the art. Thus, U.S. Pat. No. 4,927,769 describes a method of enhancing the chemiluminescent signal generated from acridinium-ester labelled conjugates by the addition of surfactants. Also, U.S. Pat. No. 4,959,182 describes a method for amplifying the chemiluminescent signal generated from alkaline phosphatase-catalyzed 1,2-dioxetanes by the addition of a surfactant and a fluorescent compound attached to it.

Known traditional methods for performing chemiluminescence assays for detection of antibodies, if utilizing enhancer compounds as herein described, usually involve separate incubation steps for reacting the sample and capture reagent, reacting the sample/capture mixture with the conjugate to which is attached an enhancer compound, and reacting the sample/capture/conjugate mixture with an enhancer-specific binding member, and then generating a signal. We have unexpectedly found that by forming a precomplex of conjugate and probe (which terms are defined hereinbelow) and performing a two-step assay as described herein, a greater readout signal is generated. This greater signal enhances assay performance which improves assay sensitivity.

SUMMARY OF THE INVENTION

This invention provides a method for determining the presence of an analyte in a test sample by specific amplification of a chemiluminescent signal generated from a heterogeneous immunoassay, which method comprises: (a) contacting a test sample containing an analyte with an analyte-specific specific binding pair member and incubating the first mixture for a time and under conditions sufficient to form analyte/analyte specific binding member pair complexes; (b) contacting the analyte/analyte specific binding member pair complexes with a precomplex comprising a pre-formed complex comprising a probe comprising an enhancer compound attached to an analyte-specific binding member and a conjugate comprising a chemiluminescent signal generating compound attached to an enhancer-specific binding member and incubating said second mixture for a time and under conditions sufficient to form a second mixture; and (e) determining the presence of the analyte in the test sample by measuring the detectable signal. The enhancer compound may be selected from the group consisting of a hapten, a fluoresecent compound and di-nitrophenol. A preferred enhancer compound is biotin, and the preferred enhancer-specific binding pair member is anti-biotin. The chemiluminescent signal generating compound may be selected from the group consisting of acridininm esters, acridinium sulfonamides, phenanthridiniums, 1,2-dioxetanes and luminol. A preferred chemiluminescent signal generating compound is an acridinium sulfonamide. Also, the analyte-specific binding pair member can be attached to a solid phase.

A kit for performing an amplied chemiluminescent assay also is provided which comprises a container containing a precomplex reagent.

BRIEF DESCRIPTION OF THE DRAWINGS

FIGS. 1A–H are graphs of the S/N and absolute signal for each sample tested, wherein:

FIG. 1A shows a three-dimensional graph of negative counts response function wherein absolute counts v. probe v. conjugate are plotted;

FIG. 1B shows a negative counts response curve wherein conjugate v. probe v. absolute counts are plotted in a line graph;

FIG. 1C shows a three-dimensional graph of a positive counts response function wherein absolute counts v. probe v. conjugate are plotted;

FIG. 1D shows a positive counts response curve wherein conjugate v. probe v. absolute counts are plotted in a line graph;

FIG. 1E shows a three-dimensional graph of a positive response function of a positive sample wherein S/N v. probe v. conjugate are plotted;

FIG. 1F shows a response curve of a positive sample wherein conjugate v. probe v. S/N are plotted in a line graph;

FIG. 1G shows a three-dimensional graph of a positive response curve of sample C33E's response function wherein S/N v. probe v. conjugate are plotted;

FIG. 1H shows a positive response curve of sample C33E wherein conjugate v. probe v. S/N are plotted in a line graph;

DETAILED DESCRIPTION OF THE INVENTION

Figure 1A:
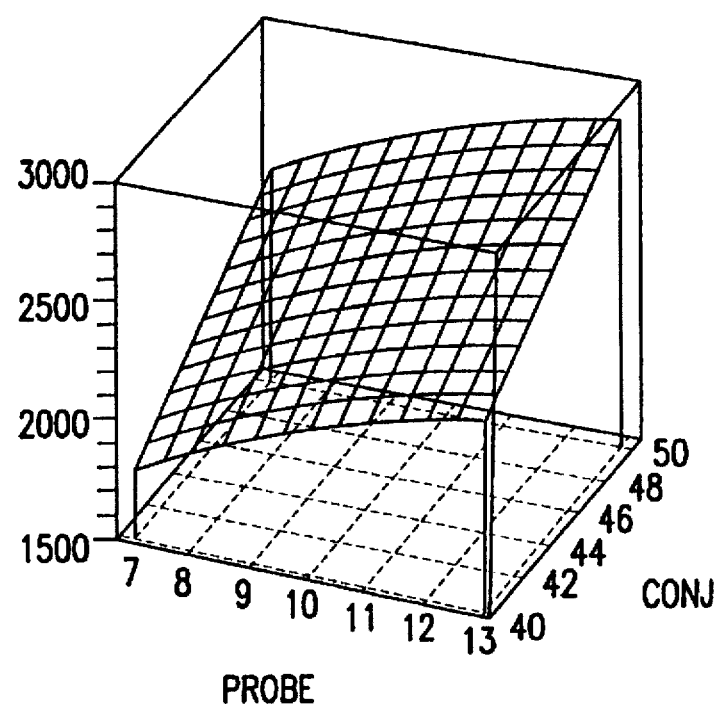

The chemiluminescent properties of acridinium compounds and their use in immunoassays has been described. Immunochemical tracers with acridininm esters or acridinium sulfonamide labels can be triggered with an alkaline peroxide solution to produce a chemiluminescent signal that maximizes after approximately two seconds. Light emission is completely extinguished after approximately ten (10) seconds. Acridinium sulfonamide labeling chemistry may be employed according to the invention for making a stable tracer of high quantum yield. This method is as described in pending U.S. patent application Ser. No. 371,763, now abandoned which enjoys common ownership and is incorporated herein by reference.

Alternatively, chemically catalyzed, long-lived 1,2-dioxetane chemiluminescence can be generated in a variety of ways. Thus, EP 0 254 051 (cited supra) describes a siloxy-substituted dioxetane as 4-(6-tert-butlydimethylsiloxy-2-naphthyl)-4-methoxyspiro[1,2-dioxetane-3,2'adamantane] that is triggered with tetrabutlyammonium chloride solution to produce a chemiluminescent signal lasting for 20 minutes. Also, enzymes such as aryl esterase and alkaline phosphatase react with aryl dioxetane derivatives stabilized with an adamantane cage to produce similar long-lived chemiluminescent signals.

Also, WO 881 00694 (WO 8906650, cited supra) describes long-lived emissions from alkaline phosphatase catalyzed reactions of 3-(2'-spiroadamantane)-4-methoxy-4-(3"-phosphoryloxy)-phenyl-1,2-dioxetanes (AMPPD) and of a similar β-galactosidase substrate. Also described is the use of these compounds in an immunoassay. Thus, alkaline phosphatase labeling techniques are known and catalyzed dioxetane chemiluminescence may be used to generate long-lived signals.

The present invention provides an immunoassay which utilizes specific binding members. A "specific binding member," as used herein, is a member of a specific binding pair. That is, two different molecules where one of the molecules through chemical or physical means specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors and enzymes, and the like. A specific binding pair member also can include a combination of a conjugate (as defined hereinbelow) and a probe (as defined hereinbelow). Furthermore, specific binding pairs can include members that are analogs of the original specific binding members, for example, an analyte-analog. Immunoreactive specific binding members include antigens, antigen fragments, antibodies and antibody fragments, both monoclonal and polyclonal, and complexes thereof, including those formed by recombinant DNA molecules. The term "hapten", as used herein, refers to a partial antigen or non-protein binding member which is capable of binding to an antibody, but which is not capable of eliciting antibody formation unless coupled to a carrier protein.

"Analyte," as used herein, is the substance to be detected which may be present in the test sample. The analyte can be any substance for which there exists a naturally occurring specific binding member (such as, an antibody), or for which a specific binding member can be prepared. Thus, an analyte is a substance that can bind to one or more specific binding members in an assay. "Analyte" also includes any antigenic substances, haptens, antibodies, and combinations thereof. As a member of a specific binding pair, the analyte can be detected by means of naturally occurring specific binding partners (pairs) such as the use of intrinsic factor protein as a member of a specific binding pair for the determination of Vitamin B12, or the use of lectin as a member of a specific binding pair for the determination of a carbohydrate. The analyte can include a protein, a peptide, an amino acid, a hormone, asteroid, a vitamin, a drug including those administered for therapeutic purposes as well as those administered for illicit purposes, a bacterium, a virus, and metabolites of or antibodies to any of the above substances. The details for the preparation of such antibodies and the suitability for use as specific binding members are well known to those skilled in the art.

A "capture reagent", as used herein, refers to an unlabeled specific binding member which is specific either for the analyte as in a sandwich assay, for the indicator reagent or analyte as in a competitive assay, or for an ancillary specific binding member, which itself is specific for the analyte, as in an indirect assay. The capture reagent can be directly or indirectly bound to a solid phase material before the performance of the assay or during the performance of the assay, thereby enabling the separation of immobilized complexes from the test sample.

The "test sample" can be a sample of biological fluid, such as whole blood or whole blood components including red blood cells, white blood cells, platelets, serum and plasma; ascites; urine; cerebrospinal fluid; and other constituents of the body which may contain the analyte of interest. Optionally, test samples may be obtained from water, soil and vegetation.

The term "probe," as used herein, means a member of the specific binding pair attached to an "enhancer compound". An "enhancer compound" can be any compound used in the assay which can enhance the signal generated by the chemiluminescent compound. Thus, enhancer compounds include haptens such as biotin, and also include fluorescein, di-nitrophenol, and the like.

The "chemiluminescent compound" is meant to include all compounds capable of generating a chemiluminescent signal such as acridinium esters, acridinium sulfonamides, phenanthridiniums, 1,2-dioxetanes, luminol, or enzymes that catalyze chemiluminescent substrates, and the like.

"Conjugate," as used herein, means a chemiluminescent compound to which a compound specific for the enhancer compound (a specific binding member of the enhancer) is attached. For example, if the enhancer compound utilized is biotin, then anti-biotin, or avidin, can be used as the enhancer-specific compound.

A solid phase may be used according to the method of the invention. A "solid phase", as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon the solid phase and which has the ability to immobilize the capture reagent through a specific binding reaction. The receptor molecule enables the indirect binding of the capture reagent to a solid phase material before the performance of the assay or during the performance of the assay.

An assay device for the present invention can have many configurations, several of which are dependent upon the material chosen as the solid phase. For example, the solid phase can include any suitable porous material. By "porous" is meant that the material is one through which the test sample can easily pass and includes both bibulous and non-bibulous solid phase materials. In the present invention, the solid phase can include a fiberglass, cellulose, or nylon pad for use in a pour and flow-through assay device having one or more layers containing one or more of the assay reagents; a dipstick for a dip and read assay; a test strip for wicking (e.g., paper) or thin layer chromatographic or capillary action (e.g., nitrocellulose) techniques; or other porous or open pore materials well known to those skilled in the art (e.g., polyethylene sheet material). The solid phase, however, is not limited to porous materials. The solid phase can also comprise polymeric or glass beads, microparticles, tubes, sheets, plates, slides, webs, tapes, test tubes, or the like, or any other material which has an intrinsic charge or which can retain a charged substance.

Natural, synthetic, or naturally occurring materials that are synthetically modified, can be used as a solid phase including polysaccharides, e.g., cellulose materials such as paper and cellulose derivatives such as cellulose acetate and nitrocellulose; silica; inorganic materials such as deactivated alumina, diatomaceous earth, $MgSO_4$, or other inorganic freely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon); porous gels such as silica gel, agarose, dextran, and gelatin; polymeric films such as polyacrilamide; and the like. The solid phase should have reasonable strength or strength can be provided by means of a support, and it should not interfere with the production of a detectable signal.

Preferred solid phase materials for flow-through assay devices include filter paper such as a porous fiberglass material or other fiber matrix materials. The thickness of such material is not critical, and will be a matter of choice, largely based upon the properties of the sample or analyte being assayed, such as the fluidity of the test sample.

To change or enhance the intrinsic charge of the solid phase, a charged substance can be coated directly to the material or onto microparticles which are then retained by a solid phase support material. Alternatively, microparticles can serve as the solid phase, by being retained in a column or being suspended in the mixture of soluble reagents and test sample, or the particles themselves can be retained and immobilized by a solid phase support material. By "retained and immobilized" is meant that the particles on or in the support material are not capable of substantial movement to positions elsewhere within the support material. The particles can be selected by one skilled in the art from any suitable type of particulate material and include those composed of polystyrene, polymethylacrylate, polypropylene, latex, polytetrafluoroethylene, polyacrylonitrile, polycarbonate, or similar materials. The size of the particles is not critical, although it is preferred that the average diameter of the particles be smaller than the average pore size of the support material being used.

According to a preferred embodiment of this invention, a test sample which may contain the analyte to be detected is contacted with a binding pair member specific for the analyte (the so-called "capture reagent"), to form a mixture. This mixture is incubated for a time and under conditions sufficient for analyte/analyte specific binding pair member complexes to form. Then, these complexes are contacted with a precomplex of a pre-formed probe/conjugate mixture (the so-termed "precomplex") comprising an enhancer compound attached to an analyte-specific binding pair member and a conjugate comprising a chemiluminescent signal generating compound conjugated to an enhancer compound binding member, to form a second mixture. This second mixture is incubated for a time and under conditions sufficient to form analyte/analyte specific binding pair member/ precomplex complexes. The presence of the analyte in the test sample is determined by measuring the signal generated by the chemiluminescent compound. Preferably, the capture reagent also may be attached to a solid phase. The preferred enhancer compound is biotin, while the preferred chemiluminescent compounds capable of generating a measurable signal are acridinium sulfonamides. The precomplex is a mixture of probe and conjugate which is reacted together (i.e., preformed complexes of probe/conjugate are made) before use in the assay. Test kits, comprising a container containing a precomplex reagent comprising a probe and conjugate. The kit also can include other reagents useful for performance of the assay, including containers of buffers for diluting sample, washing and mixing, and compounds which can trigger the chemiluminescent reaction, such as an alkaline peroxide activator solution when using acridinium compounds.

The present invention will now be described by way of examples, which are meant to illustrate, but not to limit, the scope and spirit of the invention.

EXAMPLES

Example 1

Preparation of Microparticles

Figure 2:
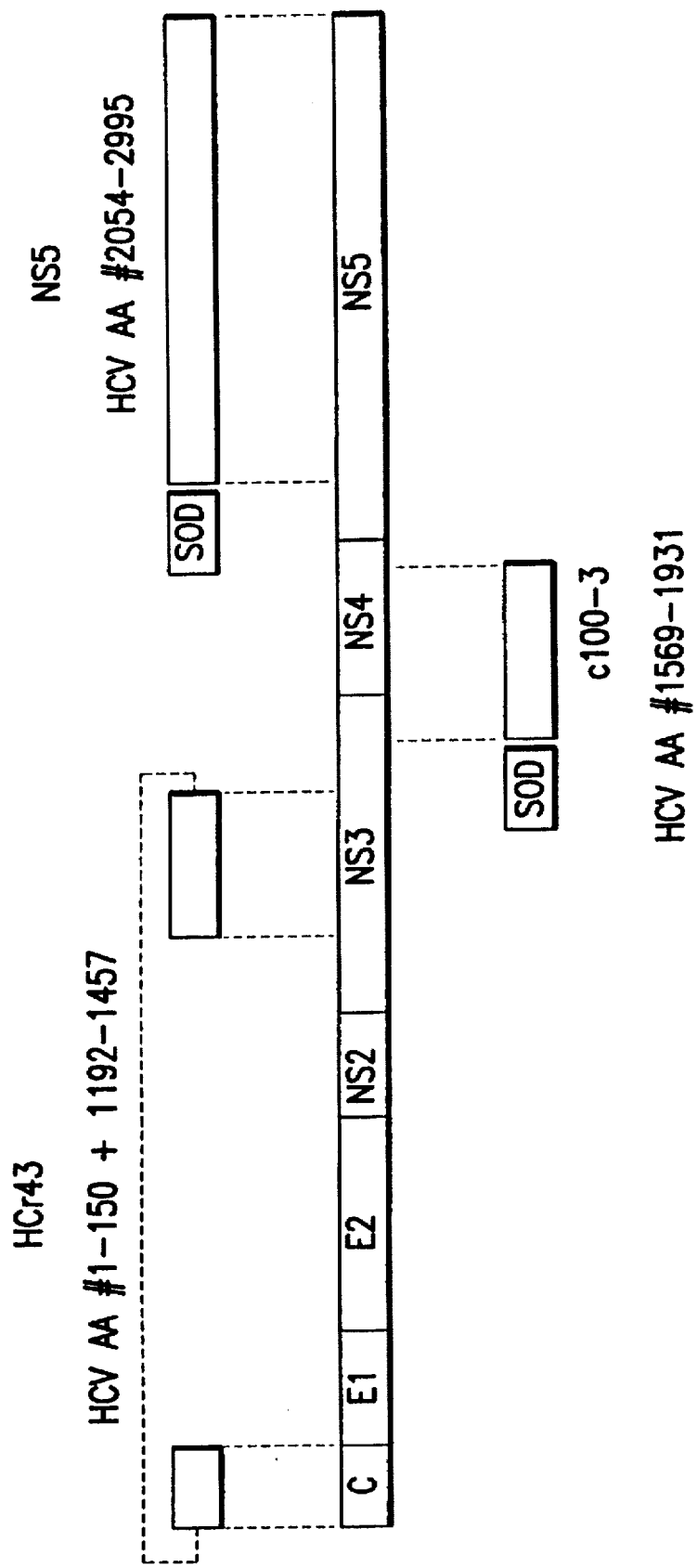
FIG. 2 is a map of the genome of HCV.

Microparticles coated with several HCV recombinant antigens were prepared by coating two separate populations of microparticles with HCV recombinant antigens cloned from the core, NS3, NS4 and NS-5 regions of HCV-1. The HCV sequence ("HCV-1") is available from GenBank®, Accession No. M62321 (*Nucleic Acid Res.* 22:3441-3444 (1994). FIG. 2 presents a genome map of HCV showing the genomic location of the recombinant antigens decribed hereinbelow.

A. Preparation of Recombinant Proteins i. HCV HC43 antigen HCV HC43 recombinant antigen was obtained from Chiron Corporation, Emeryville, Calif. It contained amino acid sequence 1–150 and 1192–1457 of HCV-1 (amino acid sequence available from GenBank®, as described hereinabove).

ii. HCV C-100 antigen. HCV C-100 recombinant antigen was obtained from Chiron Corporation, Emeryville, Calif. It contained amino acid sequence 1569–1961 of HCV-1 (available from GenBank®, as described hereinabove).

iii. HCV NS5 antigen. HCV NS5 recombinant antigen was obtained from Chiron Corporation, Emeryville, Calif. It contained amino acid sequence 2054–2995 of HCV-1 (available from GenBank®, described hereinabove).

B. Coating of Microparticles i. Preparation of HCV HC43/C100 Microparticles

Microparticles coated with both HC43 and c-100 were prepared in the following manner. Briefly, a 500 µl aliquot of microparticles (10% weight/volume, 0.7–0.9/µm) (available from Seradyne, Indianapolis, Ind.) was mixed with 962 µl of a coating buffer (20 mM phosphate, pH 5.0 with 0.1% Tween-20®) for approximately 1 minute at room temperature. Then, 154 µl of an HCV C100-3 antigen solution (0.65 mg/ml) prepared as described in Example 1(A)(ii) and 308 µl of an HC43 antigen solution (650 ug/ml) prepared as described in Example 1(A)(i) were added to the microparticle solution, mixed and tumbled for 16 hours at room temperature.

The so-prepared microparticles then were pelleted at 12,000 rpm for 10 minutes in a TD$_x$® microfuge (Abbott Laboratories, Abbott Park, Ill.). The supernatant then was removed and the microparticles were resuspended in two (2) ml of a microparticle storage buffer (MSB) (10 mM phosphate, pH 7.7, 16 mM EDTA, 3 mM dithiothreitol, 150 mM NaCl and 0.05 mg/ml sodium dodecyl sulfate [SDS]), centrifuged, the supernatant was decanted and the microparticles were again resuspended in MSB, centrifuged and the supernatant was decanted. The microparticles then were resuspended in 2.5 ml of MSB at a final concentration of 2.0%.

ii. Preparation of HCV NS-5 Microparticles

530 µl of an HCV NS-5 coating/storage buffer (50 mM carbonate, pH 10, 0.2 mg/mL SDS) and 200 µl of a 10% weight/volume 0.7–0.9 µm microparticles (available from Seradyne, Indianapolis, Ind.) were mixed and 270 µl of the HCV NS-5 antigen solution (concentration of 650 ug/mL) prepared as described in Example 1(A)(iii) was added to the microparticles. The microparticles were mixed and tumbled for 16 hours at room temperature.

The so-prepared microparticles then were pelleted at 12,000 rpm for 10 minutes in a TD$_x$® microfuge (Abbott Laboratories, Abbott Park, Ill.). The supernatant then was decanted and the microparticles were resuspended in 5 ml of MSB at final concentration of 0.4%.

iii. Blending of HCV HC43/C100 and HCV NS5 Microparticles

220 µl of microparticles prepared as described in Example 1B(i) and 330 µl of microparticles prepared as described in Example 1B(ii) were mixed together, incubated for 15 minutes and diluted to 50 ml in MSB.

Example 2

Preparation of Acridinium-Labeled Anti-Biotin Antibody

A. For Use in Three-Step Assay (i) Activation of Methyl Acridinium

An aliquot of an acridinium methyl ester (10-methyl-n-tosyl-n-(2-carboxyethyl)-9-acridinium carboxamide trifluoromethyl sulfonate (1.8 mg) (prepared as described in E.P.O. 0 273 115, published Jul. 6, 1988, incorporated herein by reference) was dissolved in 180 µl dimethylformamide (DMF, Pierce Chemical Co., Rockford, Ill.). The acridinium ester was activated by adding 88 µl of N-hydroxy succinimide (NHS, 5.75 mg/mL in DMF) and 88 µl of 1-ethyl-3-(3-dimethylaminopropyl) carbodiimide (EDAC, 9.75 mg/ml in DMF) to the dissolved acridinium. The molar ratio of EDAC to NHS was 1:1. The reaction was stirred at room temperature overnight in a light protected vial. Activation was confirmed by thin layer chromatography (TLC Silica Gel 60 F-254, Merck Darmstadt, Germany) using chloroform, DMF, and acetic acid as the developing solvent in 9:9:2 volume/volume ratio. The activated ester appeared as a new species with a greater Rf(~0.22) than the acridinium salt dissolved in DMF.

(ii) Conjugation of Anti-Biotin to Activated Methyl Acridinium

Thirty-six (36) µl of a conjugate buffer (CB, containing 0.1M sodium phosphate, 0.15M NaCl, 0.5% (3-[(3-cholamidopropyl)-dimethylammonio]-1-propane-sulfonate) (CHAPS®, Sigma Chemical Company, Saint Louis, Mo.), pH8.0) and 8 µl of activated methyl acridinium ester solution (10 mg/mL) (prepared as described in Example 2A) was added to 200 µl of a 10 mg/ml concentration of a monoclonal anti-biotin antibody (*Clinical Chemistry* 40 [11]:2112 [1994]) at room temperature while stirring in an amber glass vial and mixed for 10 minutes. The reaction mixture then was centrifuged at 12,000 rpm for two minutes in a TD$_x$® microfuge (Abbott Laboratories, Abbott Park, Ill.) to remove aggregates. The supernatant next was applied to a 300×7.8 mm Bio-Sil™ SEC-250 gel filtration column (Bio-Rad Richmond, Calif.) which had been equilibrated with buffer containing 0.1 mg/ml CHAPS, 120 mM NaCl and 10 mM sodium phosphate, pH 6.3. The column was eluted at 1.0 ml/min with the same buffer using a Beckman 421A controller equipped with a model 114M pump. Fractions of one ml were collected and the absorbance determined at 280 nm and 370 nm with a Beckman DU-7 spectrophotometer. The extent of acridinium incorporation was calculated by measuring the protein concentration using the absorbance at 280 nm corrected for the contribution made by acridinium at this wavelength (corrected protein absorbance=$A_{280}$-($A_{370}$X0.247). Moles of acridinium and IgG were calculated using molar extinction coefficients of 14,650 and 220,000 $M^{-1}cm^{-1}$, respectively. The acridinium to IgG ratio (mole/mole) obtained was about 2. The conjugate was stored 4° C.

B. For Use in Two-Step Assay (i) preparation of Pre-complexed Biotinylated Anti-human F(ab')$_2$ and Acridinium-labeled Anti-biotin Conjugate.

(a) Methyl Acridinium was labeled to anti-biotin as described in hereinabove in Example 2(A)(i). Biotinylated F(ab')$_2$ fragment of anti-human IgG was purchased from Kirkergard and Perry (Gaithersburg, Md.). The degree of functional biotin incorporated to this biotinylated probe was determined by fluorescence polarization following the method described in *Clinical*

*Chemistry* 40 (11):2112 (1994) and was found to be 8 moles biotin/mole of IgG.

Methyl acridinium labeled anti-biotin antibody was allowed to react with biotinylated F(ab')₂ probe to make a pre-complex by adding 200 µl of anti-biotin methyl acridinium (225 ug/ml) to 10 µl of biotinylated probe (1 mg/ml), and the reaction mixture and by diluting this mixture with 290 µl of conjugate diluent (containing 0.04 g/ml bovine serum albumin (BSA), 0.01 g/mL Triton X-100®, 600 mM NaCl, 0.001 g/ml sodium azide in 10 mM phosphate, pH 6.3). This mixture was left at room temperature in the dark with occasional shaking for 30 minutes. Then, 100 µl of the mixture was diluted with 159.9 ml of CB, mixed and stored overnight at room temperature. This so-formed pre-complex was filtered through a 0.2 µm Nalgene® membrane. The filtered precomplex was stored at 2°–8° C. in the dark.

(b) Equal volumes of biotinylated probe (at 10 µg/400 ml in conjugate diluent) prepared as described hereinabove was mixed with acridinium labeled conjugate (at 45 ug/400 mL in conjugate diluent) to form a reaction mixture. This reaction mixture was stirred for 2 hours at room temperature in the dark. The reaction mixture then was filtered through a 0.2 µm membrane and stored at 2°–8° C. in a colored polypropylene bottle.

Example 3

Three-Step Assay to Detect Anti-HCV Antibodies

The three-step assay was performed by using a prototype instrument (Abbott Prism™ instrument, Abbott Laboratories, Abbott Park, Ill.) as described herein. This instrument and related reagents, methods and disposable devices are described in detail in U.S. Pat. Nos. 5,089,424 and 5,120,199, as well as 5,006,309, 5,198,368, 5,232,669, 5,244,630, 5,246,354, 5,299,446, 5,015,157 and Des. 332, 834, which are commonly owned and incorporated herein by reference.

Briefly, 100 µl of a control or serum or plasma sample and 50 µl of HCV antigen coated microparticles prepared as described in Example 1 (B) (iii) were dispensed into an incubation well of a reaction tray at station 1 of the Prism™ instrument, and the assay timing was started. Sample and microparticles were mixed by mutual diffusion of each solution into the other without external agitation or shaking. The reaction mixture then was transferred to a detection well which housed a fibrous matrix at station 4 and washed after 18 minutes of incubation at room temperature. The detection well moved to the next station (station 5), where 50 µl (2.5 ng) of a biotinylated F(ab')₂ fragment of goat anti-human IgG (available from Kirkegaard & Perry, Gaithersburg, Md.) was dispensed into the fibrous matrix. The detection well was incubated for 5.4 minutes, and the microparticles and any excess probe were washed four times with 100 µl of probe wash solution (WS, containing 0.1M citrate, pH 4.5, with 0.3% LDS, 0.9% NaCl, 0.1% ProClin 300® [available from Rohn Haas Corp., Pennsylvania) at station 6. At station 7, 50 µl of acridinium labeled anti-biotin conjugate (3.5 ng) was dispensed to the fibrous matrix of the detection well in the reaction tray. The tray was further incubated, and transferred microparticles and excess conjugate were washed at station 8. The chemiluminescence (CL) signal was triggered by addition of 50 µl of an alkaline peroxide activator solution. The signal was measured at station 9 by photon counting. Signal integration time was 6 seconds. Results were originally expressed as a ratio of signal to noise (S/N) and later expressed as a ratio of signal to cut-off (S/CO).

Example 4

Two-Step HCV Assay

A two-step assay was developed and then performed as set forth in Example 3 with the following modifications. Generally, at station 1, 50 µl of control or sample, 50 µl of specimen diluent buffer (SDB, 0.1M Phosphate buffer, pH 7.0, containing 0.15% Tween 20® (available from Atlas Chemical, San Diego, Calif.), 10% newborn calf serum, 1M NaCl, 4.5% Tween-20® (available from Atlas Chemical, San Diego, Calif.), 75 µg/ml superoxide dismutase(SOD), 0.15% *E. coli* lysate and 0.1% azide), and 50 µl of HCV antigen coated microparticles (prepared as described in Example 1 (B) (iii) ) were dispensed into each incubation well and assay timing was started. These were mixed by mutual diffusion of each into the other without external agitation or shaking to form a reaction mixture. At station 4, the reaction mixture was transferred to a detection well which contained a fibrous matrix and washed twice with 300 µl of transfer wash (TW, containing 0.1M borate buffer, pH7.0, with 0.5M NaCl, 0.1% Tween-20®, 10% glycerol and 0.1% ProClin 300®) after 18 minutes of incubation at room temperature. At station 5, 50 µl of a pre-complexed biotinylated F(ab')₂/acridininm labeled anti-biotin, (biotinylated F(ab')₂ fragment of goat anti-human IgG and acridinium labeled anti-biotin antibody), was dispensed into the fibrous matrix of the detection well. The well was incubated for 22.3 minutes, and the fibrous matrix containing the reaction mixture was washed six times with 50 µl of final wash (FW, containing 0.025M MES [2-[N-morpholino] ethanesulfonic acid), pH 5.7, with 0.9% NaCl and 0.1% ProClin 300®) at station 8. The CL signal was triggered and measured at station 9. Signal integration time was 6 seconds.

Example 5

Optimization of Pre-complex by Using Various Concentrations of Probe and Conjugate Several preparations of the pre-complex mixture were made by following the procedures set forth in Example 2(B)(i)(b) and varying the ratio of probe and conjugate used. The final volume of each mixture was 166 ml. The relative performance for the preparations of precomplex using various concentration of probe and conjugate in the HCV assay was assessed by comparing the absolute chemiluminescence (CL) signal and the S/N ratio against a panel of HCV plasma samples of known reactivity. This plasma panel consisted of a recalcified human plasma positive for HCV antibodies (termed "PC"), a human plasma borderline positive for only anti-HCV 33C (termed "C33E"), a plasma sample positive for multiple antibodies of HCV diluted 1:50 in negative human plasma (termed "2257"), and a human plasma negative for HCV antibodies (termed "Negative"). Reactivity to individual HCV antibodies, reported hereinabove, was determined by performing an assay in the Abbott Matrix® HCV assay (Abbott Laboratories, Abbott Park, Ill.). All panel samples were negative for anti-HIV 1 and anti-HIV 2, anti-HTLV I and anti-HTLV-II, anti-HBc and HBsAg by FDA-approved screening assays. The results of this comparison testing are displayed below in Table 1. The results are expressed as S/N corrected for the background as shown by the calculation below, except for the negative control which is represented in absolute counts. The S/N was determined by the formula:

$$S/N = \frac{\text{Average of Sample}}{\text{Average of Negative)}}$$

The average chemiluminescence counts of four specimens was used to determine each average (n=4). A S/N≧3 to 5 was considered reactive.

TABLE 1

S/N[1] Using Pre-Complex with Various Probe and Conjugate Combinations

| Sample | Probe µg | Conjugate (µg) 40 | 45 | 50 |
|---|---|---|---|---|
| PC | 5 | | 39.87 | |
| C33E | | | 3.78 | |
| 2257 | | | 7.72 | |
| Negative | | | (1622.75) | |
| PC | 7 | 32.85 | 42.39 | 31.21 |
| C33E | | 3.29 | 3.88 | 2.9 |
| 2257 | | 7.00 | 5.65 | 6.37 |
| Negative | | (2137.25) | (2129.00) | (2496.75) |
| PC | 10 | 30.40 | 44.14 | 27.91 |
| C33E | | 3.88 | 4.55 | 2.54 |
| 2257 | | 6.09 | 8.19 | 6.25 |
| Negative | | (1919.75) | (2095.75) | (2530.25) |
| PC | 13 | 36.94 | 24.25 | 35.01 |
| C33E | | 3.87 | 2.72 | 3.67 |
| 2257 | | 8.46 | 4.52 | 6.94 |
| Negative | | (2093.00) | (2971.00) | (2906.75) |
| PC | 20 | | 36.8 | |
| C33E | | | 4.2 | |
| 2257 | | | 7.6 | |
| Negative | | | (2394.00) | |

[1]The S/N is the average chemiluminescence counts (n = 4) of the test sample divided by the average chemiluminescence counts of the negative sample (n = 4), except for the Negative, which is represented in absolute counts.

The data shown in Table 1 was analyzed by the Statgraphics® software package (available from Manucristics, Inc., Rockville, Md.) using a two factor, three level full factorial screening analysis. The analysis modeled the observed effect of variation of the amount of probe and the amount of conjugate (two factors) at each of three volumes (three levels): 7, 10 or 13 µg, or 40, 45 and 50 µg, respectively, and fitted these effects to a second order (parabolic) equation for each factor. The combinations of 5 and 20 µg probe with 45 µg conjugate were not included in the model fitting data set, but rather are illustrated in Table I for comparative purposes. The software package interpolated for values between the actual sample points. A 3-D graph of the resultant model revealed the behavior of S/N and absolute signal for each sample tested. These results are displayed in FIGS. 1A–1H.

Figure 1B:
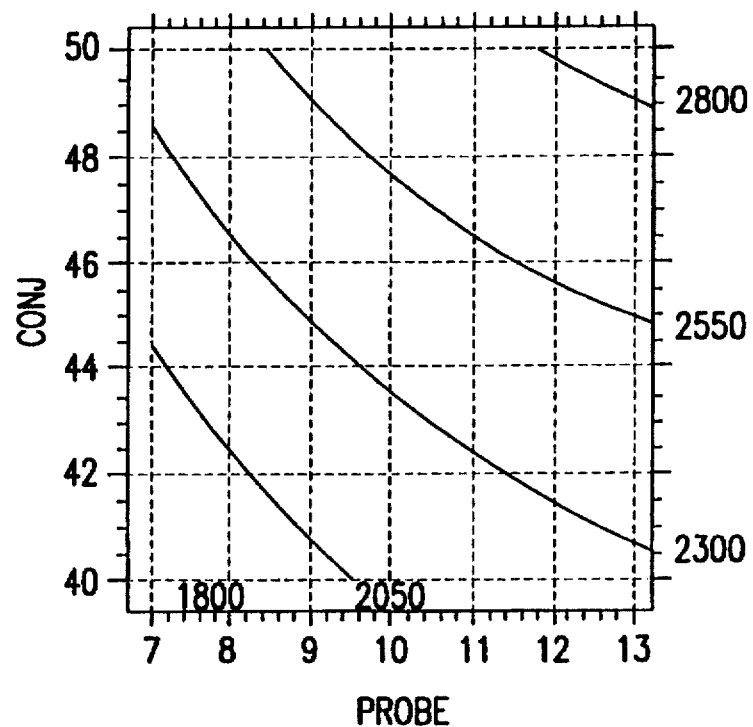
Figure 1C:
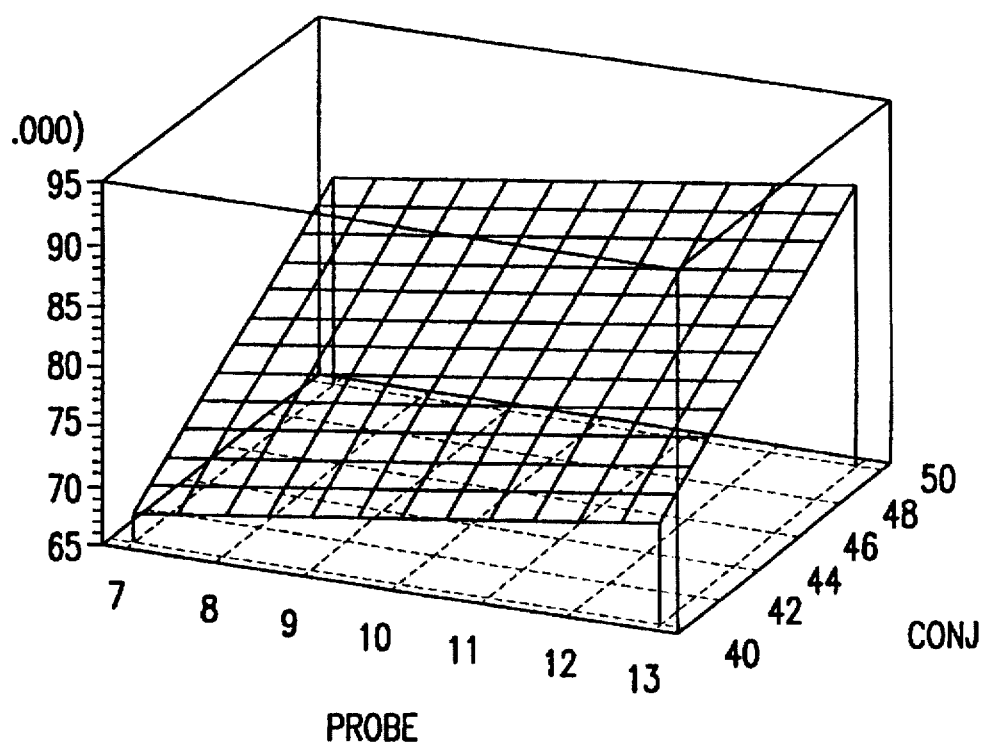
Figure 1D:
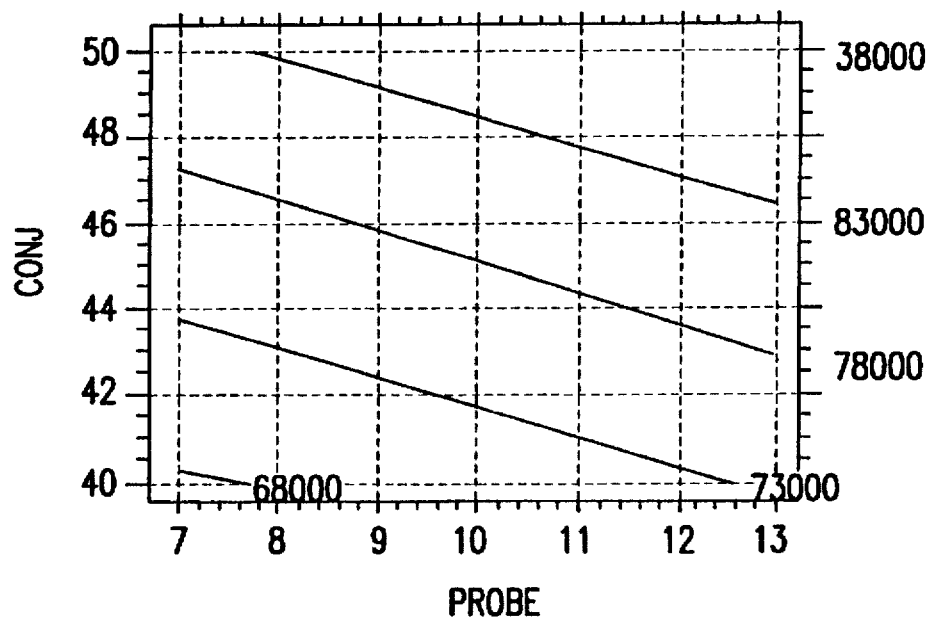
Figure 1E:
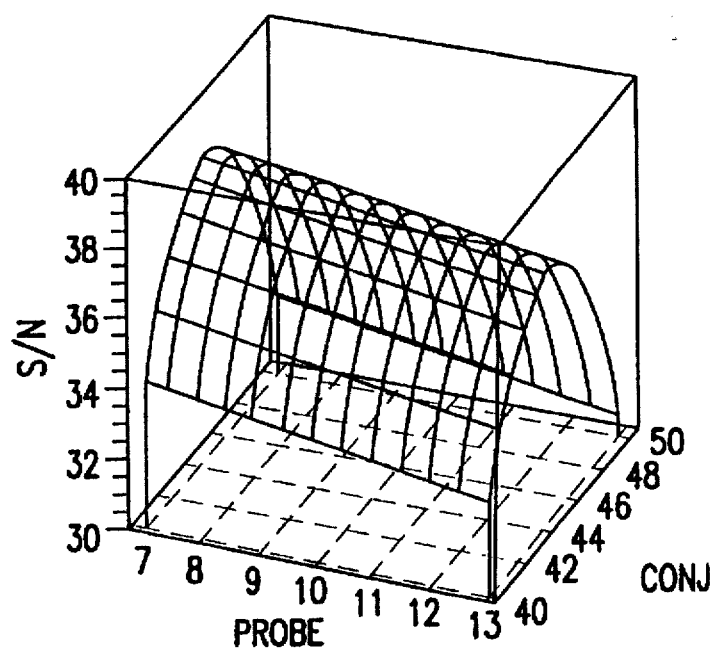
Figure 1F:
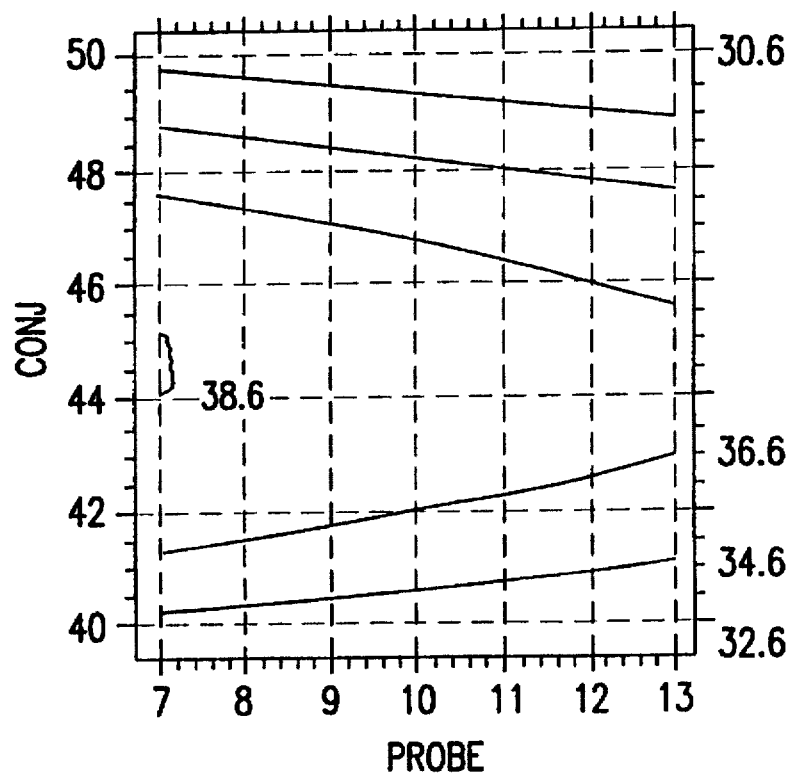
Figure 1G:
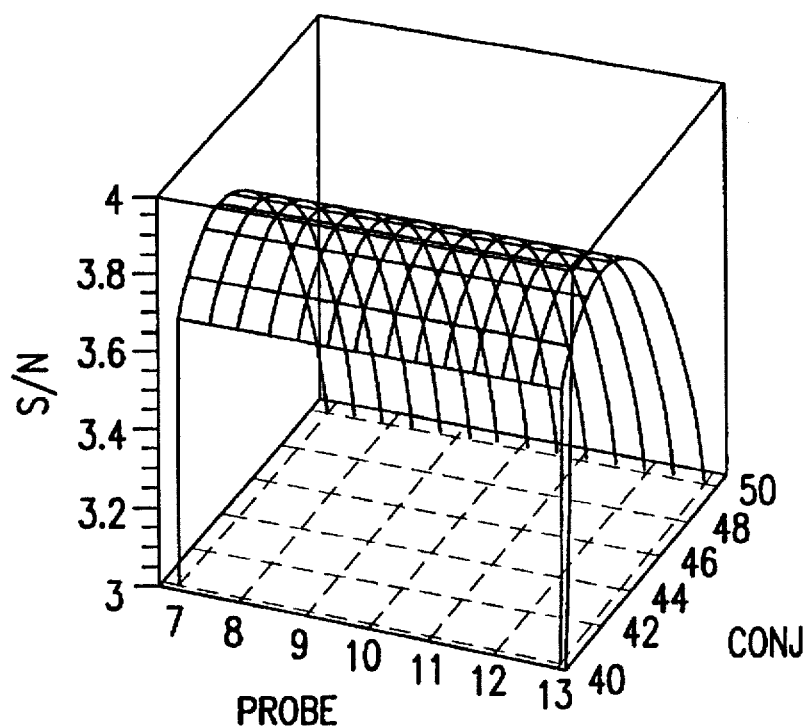
Figure 1H:
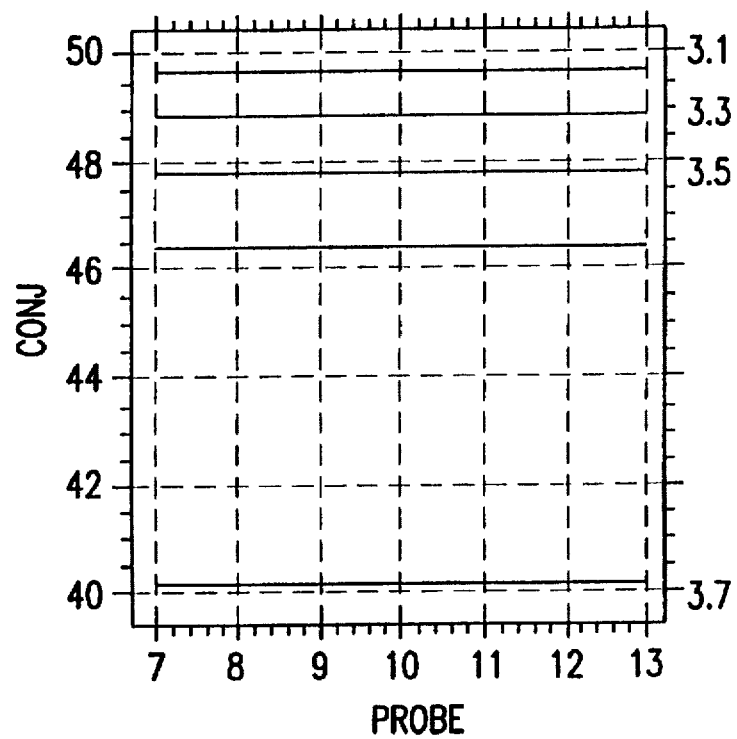

FIGS. 1A AND 1B demonstrate that by increasing the concentration of conjugate, the background also increased. As shown in FIGS. 1C and 1D, the absolute chemiluminescence count rate of the PC sample continued to increase as both the conjugate and probe volumes increased. As shown in FIGS. 1E–1H, the highest S/N for the PC and C33E plasma samples was observed at the middle concentration (45 µg) of conjugate and low concentrations (7 or 10 µg) for probe.

Example 6

Comparison of a Two-Step and a Three-Step Assay by a Panel of HCV Seroconverters The relative performance of the two-step and the three-step HCV assay described hereinabove in Examples 3 and 4 was evaluated by comparing the signal to cut-off (S/CO) against an HCV seroconversion panel of plasma samples from three individuals undergoing HCV seroconversion. Plasma samples were drawn at various time intervals. The results of this study are shown in Table 2 wherein the results are expressed as S/CO corrected for the background. For comparative purposes, the results of assying these samples with the Abbott 3.0 HCV EIA and Abbott Matrix™ HCV Assay are shown. As the data demonstrate, the two-step assay gave a higher S/CO than the three-step assay, demonstrating the superiority of the two-step assay for HCV testing.

TABLE 2

Comparison of Two-Step and Three-Step Assays by a Panel of HCV Seroconvertors

| Panel Member | Sample Date | Abbott HCV 3.0 EIA (S/CO) | Abbott Matrix ™ HCV | Three-Step (S/CO)[1] | Two-Step (S/CO)[1] |
|---|---|---|---|---|---|
| 20830D (4812) | 22 Aug | 0.31 | None | 0.3 | 0.2 |
| | 29 Aug | 0.37 | None | 1.1 | 3.6 |
| | 08 Sep | 3 | Core | 1.2 | 5.6 |
| | 28 Sep | 7.7 | 33C/C100/Core | 1.2 | 6.3 |
| | 26 Oct | 8.2 | 33C/C100/Core | 1.5 | 5.9 |
| 2190D (4813) | 19 Aug | 0.4 | NS5 | 1.4 | 2.6 |
| | 30 Aug | 0.7 | NS5/Core | 0.9 | 3.0 |
| | 28 Sep | 6.3 | 33C/C100/NS5 | 1.1 | 4.2 |
| | 19 Nov | 6.6 | 33C/C100/NS5 | 1.6 | 3.9 |
| | 22 Nov | 8.2 | 33C/C100/NS5 | 1.5 | 5.3 |
| 2528 (3535639) | 07 Feb | 0.25 | None | 0.4 | 0.2 |
| | 12 Feb | 0.45 | None | 0.4 | 0.3 |
| | 14 Feb | 0.58 | Core | 0.6 | .6 |
| | 19 Feb | 0.93 | ND[2] | 0.8 | 1.5 |
| | 21 Feb | 0.93 | 33C/C100 | 1.0 | 1.8 |
| | 26 Feb | 2.5 | 33C/C100 | 1.3 | 3.7 |
| | 28 Feb | 3.3 | 33C/C100 | 1.3 | 4.6 |
| | 04 Mar | 3.5 | 33C/C100 | 1.6 | 4.6 |

[1]Sample mean counts/5 × Negative control mean counts
[2]ND = Not Done

Example 7

Comparison of 2-Step and 3-Step Assays By a Panel of Serological HCV Samples

The relative performance of the two-step and three-step HCV assays was evaluated by comparing the results of the S/CO obtained from each format against a panel of aberrant HCV serologic samples. The assays were performed by following the procedures set forth in Examples 3 and 4. The plasma panel consisted of samples from individuals non-reactive by Abbott Matrix™ for the indicated HCV markers shown in Table 3 as well as samples from individuals reactive by Abbott Matrix™ for the indicated HCV markers shown in Table 3. The samples tested were sample number 2257 (termed "2257"), a positive control, a negative control, a negative control sample which was heat stressed (designated "NC" and tested at 56° C.), a sample positive only for HCV-Core antigen (designated as "HCV-Core"), a sample positive only for HCV-C100 (designated as "HCV-C100"), a sample positive only for HCV-C33 (designated as "HCV-C33") and a specificity sample, designated as "Spec. Sample". Samples HCV-Core, HCV-C100, and HCV-C33 were tested as various dilutions, as indicated in Table 3. The results of this study are shown in Table 3. The results are expressed as S/CO corrected for the background. As the data in Table 3 show, the two-step assay gave a higher S/CO in tests of samples except for the negative control and the specificity sample. The negative control which was heat stressed showed a lower S/CO at day 6 in the two-step assay as compared to the three-step assay.

TABLE 3

Comparison of Assays With a Panel of Aberrant HCV Serologic Samples

| Panel Member | Abbott Matrix ™ | Three-Step (S/CO) | Two-Step (S/CO) |
| --- | --- | --- | --- |
| 2257 (50X dil) | Multiple | 1.1 | 2.2 |
| Positive (100X dil) | Multiple | 2.0 | 9.3 |
| Negative | — | 0.2 | 0.2 |
| NC-heat stress, 56° C., Day 0 | — | 0.2 | 0.2 |
| NC-heat stress, 56° C., Day 6 | — | 0.6 | 0.4 |
| HCV Core (65X dil) | Core | 1.6 | 6.3 |
| HCV Core (275X dil) | Core | 1.0 | 2.0 |
| HCV Core (400X dil) | Core | 0.9 | 1.1 |
| HCV-C100 (4X dil) | C100 | 2.5 | 8.6 |
| HCV-C100 (13X dil) | C100 | 2.4 | 8.0 |
| HCV-C100 (36X dil) | C100 | 2.3 | 4.7 |
| HCV-C100 (144X dil) | C100 | 1.5 | 2.2 |
| HCV-C33 (5X dil) | C33 | 2.3 | 7.4 |
| HCV-C33 (18X dil) | C33 | 2.0 | 7.2 |
| HCV-C33 (70X dil) | C33 | 2.0 | 7.4 |
| HCV-C33 (280X dil) | C33 | 1.4 | 2.4 |
| HCV-C33 (1120X dil) | C33 | 0.9 | 1.2 |
| Spec. Sample (1) | — | 0.5 | 0.5 |
| Spec. Sample (2) | — | 0.2 | 0.2 |

Spec. Sample = Specificity Sample: For S/CO, (CO = 5 × NC)

Example 8

Stability of Precomplex (Probe and Conjugate)

Figure 3:
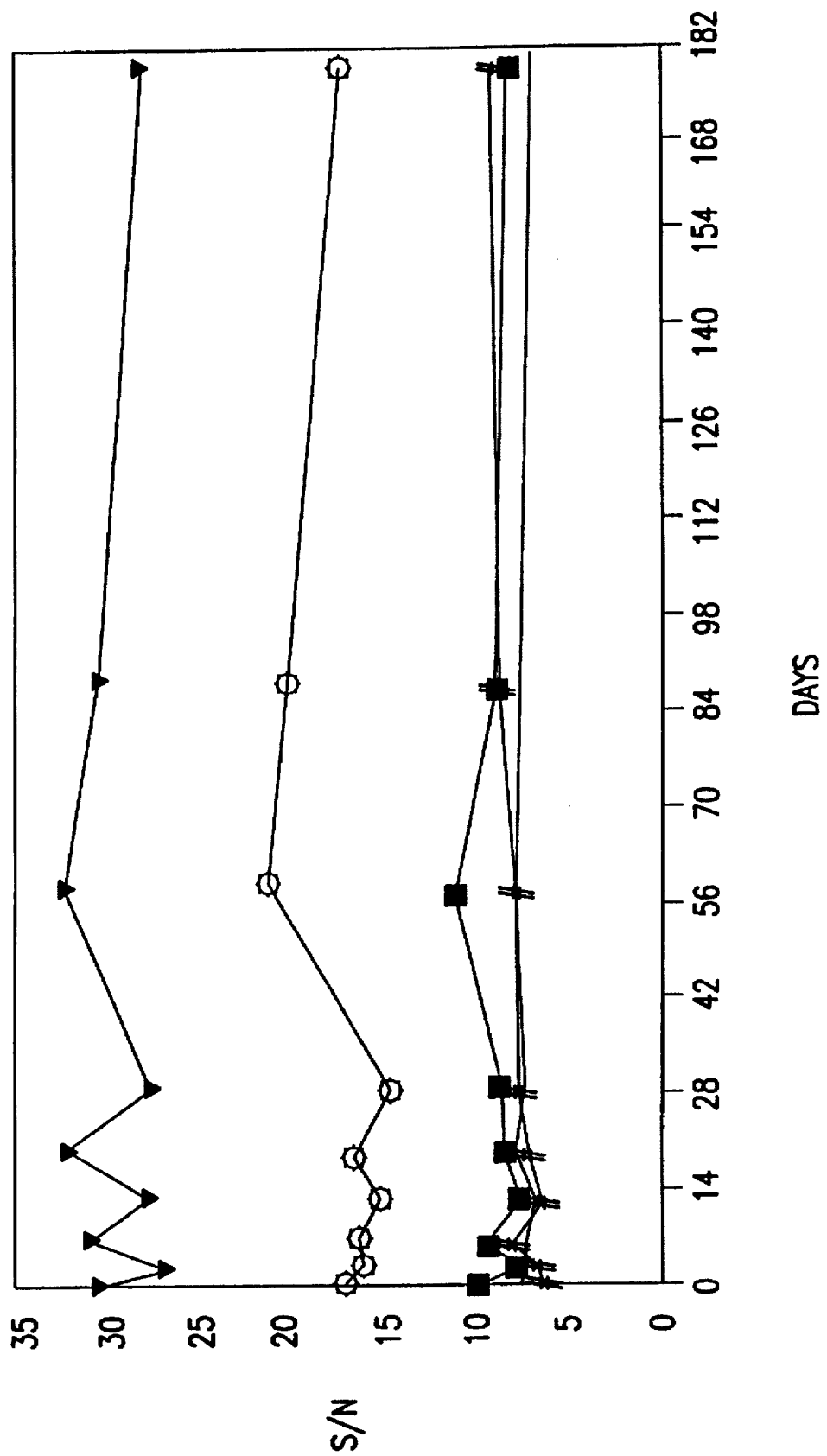
FIG. 3 is a graph of the stability of the precomplex (probe and conjugate) over a six-month period of time at 2° C. to 8° C., wherein S/N is plotted against days, and wherein a solid line between closed triangles is a graph of the positive control; a solid line between closed squares is a graph of a sample borderline positive for antibody to HCV C33; a solid line (alone) is a graph of a sample borderline positive for antibody to HCV C100; a solid line between open stars is a graph of a sample positive for antibody to HCV Core; and a solid line between open slashes is a graph of a sample positive for antibody to NS5.

The precomplex formed according to Example 2 was stored at 2° C. to 8° C. for a period of six months and tested periodically following the two-step assay described in Example 4 against various positive samples. The samples tested were a positive control (sample positive for multiple antibodies to HCV), a sample low positive for antibodies to HCV C33, a sample low positive for antibodies to HCV C100, a sample positive for antibodies to HCV Core and a sample positive for antibodies to HCV NS5. The data are presented in FIG. 3, wherein the S/N is plotted against the number of days. As the data show, the precomplex was stable over a period of 182 days (6 months) when stored at 2°–8° C., as demonstrated by only a slight decrease in S/N over this period of time against each sample tested.

The use of a precomplex thus eliminates the separate steps of antigen and antibody addition, as well as a step of washing the probe complex mixture, thus saving time and costs. Also, the use of a precomplex enhances assay sensitivity, as shown by the data detailed herein. As the data also suggests, lower concentrations of probe and conjugate are necessary, which results in efficient use of assay reagents. Finally, the precomplex is stable, showing acceptable stability data over a period of six months when stored at 2°–8° C.

Other modifications and variations of the specific embodiments of the invention as set forth herein will be apparent to those skilled in the art. Accordingly, the invention is intended to be limited in accordance with the appended claims.

What is claimed is:

1. A method for determining the presence of a Hepatitis C Virus (HCV) analyte in a test sample by specific amplification of a chemiluminescent signal generated from a heterogeneous immunoassay, comprising:

a. incubating a test sample containing a HCV analyte with an analyte-specific binding pair member for a time and under conditions sufficient to form analyte/analyte specific binding member pair complexes;

b. contacting the analyte/analyte specific binding member pair complexes with a precomplex wherein said precomplex comprises 1) a probe comprising an enhancer compound attached to an analyte-specific binding member and 2) a conjugate comprising a chemiluminescent signal generating compound attached to an enhancer-specific binding member, and incubating said second mixture for a time and under conditions sufficient to form analyte/analyte specific binding member pair/precomplex complexes wherein said chemiluminescent signal generating compound is an acridinium compound or a derivative thereof;

c. separating said resulting analyte/analyte specific binding member pair/precomplex complexes of step b from free, unbound precomplexes; and d. determining the presence of the HCV analyte in the test sample by measuring the detectable signal.

2. The method of claim 1 wherein said analyte is an antibody or an antigen.

3. The method of claim 1 wherein said enhancer compound is selected from the group consisting of a hapten, a fluoresecent compound and di-nitrophenol.

4. The method of claim 1 wherein said enhancer compound is biotin.

5. The method of claim 1 wherein said acridinium compound is selected from the group consisting of an acridium ester and an acridinium sulfonamide.

6. The method of claim 1 wherein said analyte-specific binding member is attached to a solid phase prior to step (a).

7. A kit for detecting an HCV analyte, comprising:

an HCV antigen; and a single container containing a precomplex reagent wherein said precomplex reagent comprises 1) a probe which comprises an enhancer compound and 2) a conjugate which comprises a chemiluminescent signal generating compound, wherein said chemiluminescent signal generating compound is an acridinium or a derivative thereof.

8. The kit of claim 7 wherein said enhancer compound is selected from the group consisting of a hapten, a fluoresecent compound and di-nitrophenol.

9. The kit of claim 7 wherein said acridinium compound is selected from the group consisting of an acridinium ester and an acridinium sulfonamide.

* * * * *